(12) United States Patent
Allgeier et al.

(10) Patent No.: US 6,376,714 B1
(45) Date of Patent: Apr. 23, 2002

(54) ENVIRONMENTALLY FRIENDLY PROCESS FOR THE HYDROGENATION OF DINITRILES

(75) Inventors: Alan M. Allgeier; Theodore A. Koch; Sourav K. Sengupta, all of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/871,102

(22) Filed: May 31, 2001

(51) Int. Cl.[7] ............................................. C07C 209/48
(52) U.S. Cl. ....................................... 564/492; 564/491
(58) Field of Search ................................. 564/492, 491

(56) References Cited

U.S. PATENT DOCUMENTS 5,900,511 A    5/1999   Sengupta et al.

FOREIGN PATENT DOCUMENTS

| EP | 0212986 B1 | 1/1994 |
|----|------------|--------|
| WO | WO00/67903 | 11/2000 |

*Primary Examiner*—Brian J. Davis
(74) *Attorney, Agent, or Firm*—Gerald E. Deitch

(57) ABSTRACT

Process for converting a dinitrile to a diamine and optionally an aminonitrile, in which a Group VIII element catalyst is treated with a modifier either before or during a substantially solvent-free hydrogenation reaction in which the dinitrile is contacted with hydrogen in the presence of the catalyst.

16 Claims, No Drawings

ENVIRONMENTALLY FRIENDLY PROCESS FOR THE HYDROGENATION OF DINITRILES

FIELD OF THE INVENTION

The present invention concerns the hydrogenation of aliphatic or alicyclic dinitriles to produce diamines and/or aminonitriles, e.g. adiponitrile to produce hexamethylenediamine and/or 6-aminocapronitrile.

BACKGROUND OF THE INVENTION

Dinitriles are common feedstocks to the chemical, pharmaceutical, and agrochemical industries. Through hydrogenation they can be converted to diamines or aminonitriles, which are used in or as polymer intermediates, surfactants, chelating agents, and chemical synthesis intermediates. As a particular example, adiponitrile can be converted to 6-aminocapronitrile and/or hexamethylenediamine by hydrogenation. Hexamethylenediamine is an intermediate in the production of Nylon 6,6. 6-Aminocapronitrile can be used as an intermediate in the production of Nylon 6.

Traditional methods of producing hexamethylenediamine include hydrogenation of adiponitrile over a reduced iron oxide or cobalt oxide catalyst at very high pressures and temperatures. One disadvantage associated with these high-pressure processes is the high cost of the equipment required to conduct them on a commercial scale. An alternative low pressure process for hexamethylenediamine production uses an active nickel catalyst, such as Raney™ Ni, which is promoted by aqueous caustic (an alkali metal hydroxide such as sodium hydroxide) and operates at about 3.1 MPa (450 psig) and about 75° C. While these conditions are comparatively milder than the high pressure process and offer savings on the capital expense associated with a commercial scale plant, they are deterred by the necessity of using caustic to maintain catalyst activity, which complicates refining and poses waste handling and potential environmental problems. As an example, sodium hydroxide, itself, cannot be disposed by incineration. An alternative method is deep-well disposal, which is environmentally undesirable.

Some commercial processes for hexamethylenediamine production from adiponitrile are conducted using Raney™ Ni catalyst with a solvent. Unlike water, solvents are undesirable from an environmental point of view, because they may result in volatile organic compound emissions (VOCs) to the atmosphere. Solvents are, also, undesirable because they necessitate recycling and the use of additional refining equipment, which increase capital cost.

U.S. Pat. No. 5,900,511 concerns a process where adiponitrile is hydrogenated to hexamethylenediamine and optionally 6-aminocapronitrile in the presence of a sponge cobalt catalyst in a reaction medium that is substantially free of caustic. While this process does operate at relatively low pressure and avoids the use of caustic, it would be desirable to develop a process with an even longer catalyst lifetime and corresponding increased catalyst productivity.

SUMMARY OF THE INVENTION

In its first aspect the present invention is a process for converting aliphatic or alicyclic dinitriles to diamines and optionally aminonitriles e.g. adiponitrile to hexamethylenediamine and optionally 6-aminocapronitrile, comprising forming a reaction mixture that comprises: (1) an aliphatic or alicyclic dinitrile e.g. adiponitrile; (2) hydrogen; (3) a catalyst comprising a Group VIII element; and (4) one or more modifiers selected from the group of compounds consisting of quaternary ammonium hydroxides, quaternary ammonium cyanides, quaternary ammonium fluorides, quaternary phosphonium hydroxides, and quaternary ammonium thiocyanides; said reaction mixture containing less than a 1:1 molar ratio of solvent to dinitrile; wherein the process is performed at a pressure and temperature sufficient to convert at least a portion of the dinitrile to a diamine and optionally an aminonitrile.

In its second aspect, the invention is a process for converting aliphatic or alicyclic dinitriles to diamines and optionally aminonitriles e.g. adiponitrile to hexamethylenediamine and optionally 6-aminocapronitrile, comprising contacting a Group VIII element-containing hydrogenation catalyst with one or more modifiers selected from the group of compounds consisting of quaternary ammonium hydroxides, quaternary ammonium cyanides, quaternary ammonium fluorides, quaternary phosphonium hydroxides, and quaternary ammonium thiocyanides to form a modified catalyst; and forming a reaction mixture comprising: (1) an aliphatic or alicyclic dinitrile e.g. adiponitrile; (2) hydrogen; (3) modified catalyst; and optionally (4) one or more modifiers selected from the group of compounds consisting of quaternary ammonium hydroxides, quaternary ammonium cyanides, quaternary ammonium fluorides, quaternary phosphonium hydroxides, and quaternary ammonium thiocyanides; said reaction mixture containing less than a 1:1 molar ratio of solvent to dinitrile; wherein the process is performed at a pressure and temperature sufficient to convert at least a portion of the dinitrile to a diamine and optionally an aminonitrile.

The use of the modifiers to maintain and/or improve the activity, selectivity and lifetime of the catalyst in the absence of large concentrations of solvent is advantageous over the use of caustic due to environmental and waste disposal concerns.

DETAILED DESCRIPTION OF THE INVENTION

According to the present invention, an aliphatic or alicyclic dinitrile can be hydrogenated to a diamine or a mixture of diamine and aminonitrile (for example adiponitrile can be hydrogenated to hexamethylenediamine or a mixture of hexamethylenediamine and 6-aminocapronitrile using a catalyst) in the absence of caustic. The process employs one or more catalyst modifiers to maintain or improve the activity, selectivity and/or lifetime of the catalyst and to reduce the overall concentration of unwanted byproducts. In the example of adiponitrile hydrogenation, hexamethyleneimine and bis(hexamethylene)triamine are unwanted byproducts. The use of modifiers such as quaternary ammonium hydroxide, cyanide, fluoride or thiocyanide salts, or quaternary phosphonium hydroxide salts is advantageous over the use of caustic due to environmental and waste disposal concerns. The modifiers of the present invention can be used instead of sodium hydroxide even in existing commercial facilities. Because the modifiers decompose to simple organic materials, under refining conditions they do not pose the waste handling and environmental concerns experienced with caustic. Specifically, these salts or the products of their decomposition may be incinerated similarly to any process organic waste stream. Unlike sodium hydroxide, the commonly used caustic, the modifiers of the present invention will not build-up in the incinerator firebricks, nor will they require disposal via deep-wells.

While this invention does not exclude the use of caustic, an environmental benefit will be garnered by avoiding its use.

Suitable aliphatic or alicyclic dinitriles, for use herein, have the general formula $R(CN)_2$, wherein R is a saturated hydrocarbylene group. A saturated hydrocarbylene group contains carbon and hydrogen atoms in branched or straight chains or rings and does not contain a double or triple bond between any pair of carbon atoms. Preferred hydrocarbylene groups contain from 2 to 25, more preferably 2 to 15, and most preferably 2 to 10 carbon atoms per group. In other words, preferred dinitriles contain from 4 to 27, more preferably 4 to about 17, and most preferably 4 to 12, carbon atoms per dinitrile molecule. The preferred type of hydrocarbylene group is a linear alkylene group.

Examples of suitable dinitriles include, but are not limited to, adiponitrile; methylglutaronitrile; succinonitrile; glutaronitrile; alpha, omega-heptanedinitrile; alpha, omega-octanedinitrile, alpha, omega-decanedinitrile, alpha, omega-dodecanedinitrile; and combinations of two or more thereof. The preferred dinitrile is adiponitrile.

The catalyst in the process is a hydrogenation catalyst suitable for hydrogenating a dinitrile to a diamine or a mixture of diamine and aminonitrile. Preferred are catalysts based on Group VIII elements including iron, cobalt, nickel, rhodium, palladium, ruthenium and combinations thereof. The catalyst may also contain one or more promoters in addition to the Group VIII elements mentioned above, for example, one or more Group VIB elements such as chromium, molybdenum, and tungsten and/or one or more Group VIII elements such as iron, cobalt, nickel, ruthenium, rhodium, palladium, and others. The promoters may be present in concentrations 0.01 to 15 percent based on the weight of the catalyst, preferably from 0.5 to 5 percent. The catalyst can also be in the form of an alloy, including a solid solution of two or more metals, or an individual metal or a sponge metal catalyst. A "sponge metal" is one, which has an extended porous "skeleton" or "sponge-like" structure, preferably a base metal (e.g. iron, cobalt or nickel), with dissolved aluminum, optionally containing promoter(s). The amount of iron, cobalt or nickel present in the catalyst may vary. Skeletal catalysts useful in the process of this invention contain iron, cobalt or nickel in an amount totaling from about 30 to about 97 weight % iron, cobalt and/or nickel, more preferably from about 85 to about 97 weight % iron, cobalt or nickel, most preferably 85–95% nickel. Sponge catalysts modified with at least one metal promoter selected from the group consisting of nickel, chromium, iron and molybdenum are particularly useful. The sponge metal catalysts also contain surface hydrous oxides, adsorbed hydrogen radicals, and hydrogen bubbles in the pores. The instant catalyst, preferably also includes from about 2 to 15 weight % aluminum, more preferably from about 4 to 10 weight % aluminum. Commercially available catalysts of the sponge type are promoted or unpromoted Raney® Ni or Raney® Co catalysts that can be obtained from the Grace Chemical Co. (Columbia, Md.), or alternative sponge metal catalysts available, for example, from Activated Metals Corporation (Sevierville, Tenn.) or Degussa (Parsippany, N.J.). Sponge metal catalysts can be produced by the method described in U.S. Pat. No. 1,628,190. Promoted sponge catalysts can be produced by the method described in PCT Application No. WO200067903 or EPO Application No. 212,986.

While the degree of beneficial effects of this invention may vary with the structure of the dinitrile and the identity of the Group VIII metal or metals incorporated in the catalyst, it is important to realize that even small improvements in selectivity can have large economic impact for large-scale industrial processes.

The catalytic metal can also be supported on an inorganic support such as alumina, magnesium oxide, and combinations thereof. The metal can be supported on an inorganic support by any means known to one skilled in the art such as, for example, impregnation, coprecipitation, ion exchange, and combinations of two or more thereof.

The catalyst can be present in any appropriate physical shape or form. It can be in fluidizable forms, extrudates, tablets, spheres, or combinations of two or more thereof. When employing the process using a fixed bed catalyst, the catalyst is in the form of granules having a particle size in the range of about 0.03 to 0.40 inch (0.76 to 10.2 mm). When employing the process using a slurry-phase catalyst, the catalyst is in finely divided form, preferably less than about 100 $\mu$ in size, most preferred range being 20 to 75 $\mu$.

The molar ratio of catalyst to dinitrile can be any ratio as long as the ratio can catalyze the selective hydrogenation of a dinitrile. The weight ratio of catalyst to dinitrile is generally in the range of from about 0.0001:1 to about 1:1, preferably about 0.001:1 to about 0.5:1. If the catalytic element is supported on an inorganic support or is a portion of alloy or solid solution, the catalytic element is generally present in the range of from about 0.1 to about 60 and preferably about 1 to about 50 weight percent, based on the total catalyst weight.

The modifiers of the present invention are selected from quaternary ammonium hydroxide, quaternary ammonium cyanide, quaternary ammonium fluoride, quaternary ammonium thiocyanides, or quarternary phosphonium hydroxide. More than one modifier may be used in the reaction. Specific examples of suitable modifiers are tetramethylammonium hydroxide, tetrabutylammonium cyanide, tetraethylammonium fluoride, tetrabutylammonium thiocyanide and tetrabutylphosphonium hydroxide. Preferred modifiers are quaternary ammonium hydroxides. Preferred quaternary ammonium hydroxides are tetraalkylammonium hydroxide compounds. Examples of suitable tetraalkylammonium hydroxide compounds are tetramethylammonium hydroxide, tetraethylammonium hydroxide, tetrapropylammonium hydroxide and tetrabutylammonium hydroxide. It should be noted that various hydrated forms such as, for example, tetramethylammonium hydroxide pentahydrate, are included within the meaning of tetraalkylammonium hydroxide and tetraalkylphosphonium hydroxide.

The hydrogenation reaction can be conducted 50–150° C., preferably 70–90° C. and 2.1–10.3 MPa (300–1500 psig) total pressure with hydrogen, preferably 2.4–3.8 MPa (350–550 psig). In a preferred mode of operation the process is conducted on a continuous basis in a continuous stirred tank reactor (CSTR) or a slurry bubble column reactor (SBCR) or a plug flow reactor (PFR), or a trickle bed reactor. An example of a bubble column reactor, which is not confined to this reaction, has been described in U.S. Pat. No 4,429,159. Descriptions of plug flow and continuous stirred tank reactors have been delineated in the book entitled, "Chemical Reaction Engineering" written by Octave Levenspiel. The preference for reactor is not meant to limit the invention, which can also be conducted in batch mode.

The process can be operated substantially in the absence of solvent. The expression "substantially in the absence of solvent" refers to an amount less than a 1:1 molar ratio of solvent to dinitrile. Preferably, the process is operated with no solvent. For the purposes of this patent, a solvent is defined as a substance, other than water, which is added to a reaction mixture and serves to solvate one or more reaction components, increases the volume of the reaction mixture, provides a medium for transferring (or removing) the heat of reaction, is not a product of the reaction and is either not incorporated in the final product or does not alter the properties of the final product. While not comprehensive, a list of solvents includes ammonia; amines, such as triethylamine; alcohols, such as methanol, ethanol, propanol, and butanol; ethers, such as tetrahydrofuran and dioxane; amides, such diethylacetamide and N-methylpyrolidinone; and esters, such as ethyl acetate and dimethyladipate.

The modifier and dinitrile may be introduced to a reactor, which contains catalyst, separately or as a premixed solution, optionally with a diamine, an aminonitrile, water, a solvent or any combination thereof. The modifier can be added in a weight ratio to dinitrile from 1:5000 to 1:50, preferably from 1:2000 to 1:500.

The yields of diamine and/or aminonitrile, e.g. hexamethylenediamine and/or 6-aminocapronitrile, depend on operating conditions including temperature, pressure, hydrogen flow rate, amount and kind of catalyst, amount of modifier, space velocity and the like. For the purpose of this invention, the term "space velocity" is defined as the unit weight of dinitrile fed into the reactor per hour, per unit weight of the catalyst. Typically, the dinitrile should be added to the reactor such that the space velocity of the dinitrile is within the range of 0.5 to 50 $h^{-1}$. Most preferred space velocities may be readily determined by those skilled in the art using conventional techniques. When the rate of dinitrile addition is below or above the herein stated space velocities, the selectivity and yield of the desired compound (s) diminish drastically, resulting in lower catalyst activity and shortened life of the catalyst.

While not meant to limit the invention by any theory, it is possible that the modifier reacts with the metallic element(s) of the catalyst forming a modifier metal complex. The resulting complex may contain the Group VIII element in its metallic state or perhaps in an oxidized state. The reaction of modifier with the catalytic element may be irreversible but more likely is a reversible equilibrium reaction. The interaction of the modifier with the catalyst may alter the reactivity of the catalyst, suppress secondary amine oligomer formation and thereby increase the lifetime of the catalyst.

The catalyst and modifier can be separately introduced into contact with dinitrile; however, the catalyst may be precontacted with the modifier. This may be done in water and/or a solvent such as an alcohol, ether, ester, ammonia, or combinations of two or more thereof. Preferably, the precontacting is also carried out in the presence of hydrogen. Contacting of the catalyst and modifier produces a pretreated catalyst. The pretreated catalyst can be washed with a solvent disclosed above, preferably under anaerobic conditions to produce a modifier-treated catalyst.

The contacting of the catalyst and modifier can be carried out under any conditions effective to produce a modifier-treated catalyst that can improve selective hydrogenation of a dinitrile to a diamine and/or aminonitrile, e.g. adiponitrile to hexamethylenediamine and/or 6-aminocapronitrile. Generally, the entire process for producing the modifier-treated catalyst can be carried out by contacting a catalyst with a modifier disclosed above at a temperature in the range of from about 20° C. to about 150° C., preferably about 30° C. to about 100° C., under the same general pressures as described earlier, for about 5 seconds to about 25 hours. The weight ratio of modifier to catalyst in the pre-contacting procedure generally ranges from about 0.01:1 to about 5:1, preferably from about 0.05:1 to about 3:1, more preferably from about 0.1:1 to about 2:1, and especially from about 0.25:1 to about 1:1.

Hydrogen can be delivered to the reaction mixture as gas, preferably pure hydrogen. The hydrogen should be delivered at a rate that will maintain hydrogen in molar excess relative to the dinitrile.

Water can be added to the reactor at a weight ratio to dinitrile from 1:10000 to 1:3, continuously or at intermittent periods to maintain catalyst selectivity, life and activity. Caustic can be added to the reactor at a weight ratio to dinitrile from 1:400,000 to 1:100, continuously or at intermittent periods to maintain catalyst selectivity, life and activity. Preferably, a small amount of caustic is added to the reaction mixture at the beginning of the reaction to extend catalyst life and improve catalyst activity. Use of caustic will undermine to some extent the environmental benefits that can be derived from this invention.

Diamine and/or aminonitrile, e.g. hexamethylenediamine and/or 6-aminocapronitrile, can be recovered from the reaction products by typical purification procedures such as recrystallization or preferably, distillation. The unreacted dinitrile can be sent back to the hydrogenation reactor to obtain additional diamine and/or aminonitrile.

In performing the process according to the invention one obtains the advantages of increased catalyst lifetime, improved selectivity to diamine and/or aminonitrile, and decreased yield to byproducts, especially amine coupling byproducts, compared to operating a process in the absence of catalyst modifiers. Additionally, one gains an environmental advantage in terms of disposal compared to a process operating with caustic sodium hydroxide.

EXAMPLES

Example 1

Batch Hydrogenation with Raney® Ni 2400 in the Presence of Tetramethylammonium Hydroxide Pentahydrate.

To a 300-cc tank reactor were added 6.01 g of Raney Ni 2400 slurry (~3.0 g dry weight), 3.0 g water, 90.0 g hexamethylenediamine (HMD), 60.0 g adiponitrile (ADN), and 0.204 g of tetramethylammonium hydroxide pentahydrate, 97% purity (TMAHP). The reactor was purged with nitrogen and pressure tested for leaks. The reactor was then purged with hydrogen. After the hydrogen purge, the reactor was pressurized to ~0.28 MPa (40 psig) with hydrogen and heated to 75° C., while being mechanically stirred at 250 RPM. Upon reaching the reaction temperature, the reactor was pressurized to 3.45 MPa (500 psig) hydrogen and stirred at 1500 RPM to commence the reaction. The initial rate of hydrogen uptake (through 20% conversion) from a 1-liter hydrogen reservoir was 0.069 MPa/min (9.96 psi/min). After 420 min, a liquid sample was withdrawn from the reactor by means of a dip tube. A sample was prepared with diethylacetamide (DEAC) as an internal standard and was analyzed by gas chromatography. The sample comprised 90.6% HMD, 0.2% 6-aminocapronitrile (ACN), 0.01% hexamethyleneimine (HMI), 0.11% bis (hexamethylene)triamine (BHMT) by weight; the ADN conversion was at 100%.

Comparative Example A

Batch Hydrogenation with Raney® Ni 2400 in the Absence of Tetramethylammonium Hydroxide Pentahydrate.

Example 1 was repeated except no TMAHP was added to the reactor.

To a 300-cc tank reactor were added 6.04 g of Raney Ni 2400 slurry (~3.0 g dry weight), 3.01 g water, 90.03 g hexamethylenediamine (HMD), and 60.00 g adiponitrile (ADN). The reactor was purged with nitrogen and pressure tested for leaks. The reactor was then purged with hydrogen. After the hydrogen purge, the reactor was pressurized to ~0.28 MPa (40 psig) with hydrogen and heated to 75° C., while being mechanically stirred at 250 RPM. The reactor was then pressurized to 3.45 MPa (500 psig) with hydrogen and stirred at 1500 RPM to commence the reaction. The initial rate of hydrogen uptake from a 1-liter reservoir was 0.053 MPa/min (7.75 psi/min). After 527 min, a liquid sample was withdrawn from the reactor by means of a dip tube. A sample was prepared with diethylacetamide (DEAC) as an internal standard and was analyzed by gas chromatography. The sample comprised 64.1% HMD, 0.7% ADN, 11.1% 6-aminocapronitrile (ACN), 3.6% HMI and 3.1% BHMT by weight; the ADN conversion was 99.3%.

Example 2

Batch Hydrogenation with Raney® Ni 2400 in the Presence of Tetrabutylammonium Cyanide.

To a 300-cc tank reactor were added 6.04 g of Raney Ni 2400 slurry (~3.0 g dry weight), 3.25 g water, 90.0 g hexamethylenediamine (HMD), 60.04 g adiponitrile (ADN) and 0.298 g tetrabutylammonium cyanide, 95% purity. The reactor was purged with nitrogen and pressure. tested for leaks. The reactor was then purged with hydrogen. After the hydrogen purge, the reactor was pressurized to ~0.28 MPa (40 psig) with hydrogen and heated to 75° C. while being mechanically stirred at 250 RPM. The reactor was then pressurized to 3.45 MPa (500 psig) with hydrogen and stirred at 1500 RPM to commence the reaction. The initial rate of hydrogen uptake from a 1-liter reservoir was 0.020 MPa/min (2.94 psi/min). After 1245 min a liquid sample was withdrawn from the reactor by means of a dip tube. A sample was prepared with diethylacetamide (DEAC) as an internal standard and was analyzed by gas chromatography. The sample comprised 81.31% HMD, 0.13% ADN, 4.24% 6-aminocapronitrile (ACN), 0.2% HMI and 0.7% BHMT; the ADN conversion was at 99.67%.

Example 3

Batch Hydrogenation with Raney® Ni 2400 in the Presence of Tetraethylammonium Fluoride To a 300-cc tank reactor were added 6.02 g of Raney Ni 2400 slurry (~3.0 g dry weight), 3.01 g water, 90.0 g hexamethylenediamine (HMD), 60.0 g adiponitrile (ADN) and 0.205 g of tetraethylammonium fluoride hydrate, 98% purity (TEAF). The reactor was purged with nitrogen and pressure tested for leaks. The reactor was then purged with hydrogen. After the hydrogen purge, the reactor was pressurized to ~0.28 MPa (40 psig) with hydrogen and heated to 75° C. while being mechanically stirred at 250 RPM. The reactor was then pressurized to 3.45 MPa (500 psig) with hydrogen and stirred at 1000 RPM to commence the reaction. The initial rate of hydrogen uptake from a 1-liter reservoir was 0.034 MPa/min (4.91 psig/min). After 1253 min a liquid sample was withdrawn from the reactor via a dip tube. At the completion of the run, a liquid sample was withdrawn from the reactor by means of a dip tube. A sample was prepared with diethylacetamide (DEAC) as an internal standard and was analyzed by gas chromatography. The sample comprised 90.74% HMD, 0.00% ADN, and 0.00% 6-aminocapronitrile (ACN), 0.3% HMI and 1.1% BHMT by weight; the ADN conversion was 100%.

Example 4

Batch Hydrogenation with Co/alumina in the Presence of Tetramethylammonium Hydroxide Pentahydrate.

To a 300 cc tank reactor were added 6.0 grams of 0.6% Ru-promoted Co/$Al_2O_3$ catalyst, 13.0 g water, 90.0 g hexamethylenediamine (HMD) 0.20 g of tetramethylammonium hydroxide pentahydrate 97% (TMAH) and 60.0 g adiponitrile (ADN). The reactor was purged with nitrogen and pressure tested for leaks. The reactor was then purged with hydrogen. After the hydrogen purge, the reactor was pressurized to ~40 psig with hydrogen and heated to 75° C., while being mechanically stirred at 250 RPM. After reaching reaction temperature, the reactor was pressurized to 500 psig hydrogen and stirred at 1500 RPM to commence the reaction. The initial hydrogen uptake rate from a 1-liter reservoir was 2.76 psi/min. After 405 min, a liquid sample was withdrawn from the reactor by means of a dip tube. A sample was prepared with diethylacetamide (DEAC) as an internal standard and was analyzed by gas chromatography. The sample comprised 78.75% HMD, 0.0% ADN and 0.0% ACN, 3.94% HMI and 6.91% BHMT; the ADN conversion was 100%.

Comparative example B

Batch Hydrogenation with Co/alumina in the Absence of Tetramethylammonium Hydroxide Pentahydrate To a 300 cc tank reactor were added 5.9 grams of 0.6% Ru-promoted Co/$Al_2O_3$ catalyst, 13.0 g water, 90.0 g hexamethylenediamine (HMD) and 60.0 g adiponitrile (ADN). The reactor was purged with nitrogen and pressure tested for leaks. The reactor was then purged with hydrogen. After the hydrogen purge, the reactor was pressurized to ~40 psig with hydrogen and heated to 75° C., while being mechanically stirred at 250 RPM. After reaching reaction temperature, the reactor was pressurized to 500 psig hydrogen and stirred at 1500 RPM to commence the reaction. The initial hydrogen uptake rate from a 1-liter reservoir was 2.78 psi/min (0.019 MPa/min). After 424 min, a liquid sample was withdrawn from the reactor by means of a dip tube. A sample was prepared with diethylacetamide (DEAC) as an internal standard and was analyzed by gas chromatography. The sample comprised 75.02% HMD, 0.0% ADN and 0.0% ACN, 5.1 % HMI and 7.7 % BHMT; the ADN conversion was 100%.

Example 5

Batch Hydrogenation of Adiponitrile with Raney® Ni 2400 in the Presence of Tetramethylammonium Hydroxide pentahydrate to form 6-Aminocapronitrile and Hexamethylenediamine To a 300-cc tank reactor were added 8.01 g of Raney Ni 2400 slurry (~4.0 g dry weight), 4.0 g water, 150.0 g adiponitrile (ADN), and 0.31 g of tetramethylammonium hydroxide pentahydrate, 97% purity (TMAHP). The reactor was purged with nitrogen and pressure tested for leaks. The reactor was then purged with hydrogen. After the hydrogen purge, the reactor was pressurized to ~0.28 MPa (40 psig) with hydrogen and heated to 75° C., while being mechanically stirred at 250 RPM. Upon reaching the reaction temperature, the reactor was pressurized to 3.45 MPa (500 psig) hydrogen and stirred at 1500 RPM to commence the reaction. The initial rate of hydrogen uptake (through 20% conversion) from a 1-liter hydrogen reservoir was 0.291 MPa/min (42.2 psi/min). After 35 min, a liquid sample was withdrawn from the reactor by means of a dip tube. A sample was prepared with N-methylpyrollidinone as an internal standard and was analyzed by gas chromatography. The sample comprised 17.2% HMD, 57.2% 6-aminocapronitrile (ACN), 0% hexamethyleneimine (HMI), 0% bis (hexamethylene)triamine (BHMT) by weight; the ADN conversion was 92%.

Example 6

Batch Hydrogenation of Octanedinitrile with Raney® Ni 2400 in the Presence of Tetramethylammonium Hydroxide Pentahydrate to Form Octamethylenediamine.

To a 100-cc pressure reactor were added 2.01 g of Raney Ni 2400 slurry (~1.0 g dry weight), 2.50 g water, 30.02 g 1,8-octanedinitrile (ODN) and 0.10 g of tetramethylammonium hydroxide pentahydrate, 97% purity (TMAHP). The reactor was purged with nitrogen and pressure tested for leaks. The reactor was then purged with hydrogen. After the hydrogen purge, the reactor was pressurized to 2.76 MPa (400 psig) and heated to 75° C., while being mechanically stirred at 700 rpm. The initial rate of hydrogen uptake (through 20% conversion) from a 1-liter reservoir was 0.014 MPa/min (2.0 psi/min). After 120 min the reaction had consumed 1.72 MPa (249 psig) of hydrogen from the reservoir. After 330 min a liquid sample was withdrawn from the reactor by means of a dip tube. An analytical sample was prepared by dilution in ethanol and analyzed by gas chromatography. The sample comprised 96.6% octamethylenediamine. The ODN conversion was 100%.

Comparative Example C

Batch Hydrogenation of Octanedinitrile with Raney® Ni 2400 in the absence of Tetramethylammonium Hydroxide Pentahydrate to Form Octamethylenediamine.

To a 100-cc pressure reactor were added 2.00 g of Raney Ni 2400 slurry (~1.0 g dry weight), 2.50 g water, and 30.02 g 1,8-octanedinitrile (ODN). The reactor was purged with nitrogen and pressure tested for leaks. The reactor was then purged with hydrogen. After the hydrogen purge, the reactor was pressurized to 2.76 MPa (400 psig) and heated to 75° C., while being mechanically stirred at 700 rpm. The reaction rapidly consumed 0.152 MPa (22 psig) of hydrogen from a 1-liter reservoir within 15 min and then drastically slowed down. After 120 min the reaction had consumed only 0.228 MPa (33 psig); essentially the reaction had stopped. A liquid sample was withdrawn from the reactor at this point by means of a dip tube. An analytical sample was prepared by dilution in ethanol and analyzed by gas chromatography. The sample comprised 2.2% octamethylenediamine, 6.0% 8-aminooctanenitrile and 91.4% 1,8-octanedinitrile.

What is claimed:

1. A process for converting dinitriles to diamines and/or aminonitriles, comprising forming a reaction mixture that comprises (1) a dinitrile; (2) hydrogen; (3) a catalyst comprising a Group VIII element; and (4) one or more modifiers selected from the group of compounds consisting of quaternary ammonium hydroxides, quaternary ammonium cyanides, quaternary ammonium fluorides, quaternary phosphonium hydroxides, and quaternary ammonium thiocyanides; said reaction mixture containing less than a 1:1 molar ratio of solvent; wherein the process is carried out at a pressure and temperature sufficient to convert at least a portion of the dinitrile to a diamine and optionally an aminonitrile.

2. The process of claim 1 wherein the temperature is 50 to 150° C., and the total pressure is about 1.38 to about 10.34 MPa (200 to 1500 psig).

3. The process of claim 2 wherein the catalyst is sponge nickel.

4. The process of claim 3 wherein the modifier is a quaternary ammonium hydroxide compound.

5. The process of claim 4 wherein the modifier is a tetramethylammonium hydroxide.

6. The process of claim 5 wherein the temperature is 70 to 90° C., and the total pressure is about to 2.07 to about 6.89 MPa (300 to 1000 psig).

7. The process of claim 6 wherein the modifier is elected from the group consisting of etramethylammonium hydroxide, tetraethylammonium hydroxide, tetrapropylammonium hydroxide, tetrabutylammonium hydroxide and tetrabutylphosphonium hydroxide.

8. The process of claim 7 wherein the weight ratio of dinitrile to modifier is in the range of about 1:5000 to about 1:50.

9. A process for converting dinitriles to diamines and/or aminonitriles, comprising contacting a Group VIII element-containing hydrogenation catalyst with a modifier selected from the group of compounds consisting of quaternary ammonium hydroxides, quaternary ammonium cyanides, quaternary ammonium fluorides, quaternary phosphonium hydroxides, and quaternary ammonium thiocyanides to form a modified catalyst; and forming a reaction mixture that comprises (1) a dinitrile; (2) hydrogen; (3) modified catalyst; and optionally (4) one or more modifiers selected from the group of compounds consisting of quaternary ammonium hydroxides, quaternary ammonium cyanides, quaternary ammonium fluorides, quaternary phosphonium hydroxides, and quaternary ammonium thiocyanides; said reaction mixture containing less than a 1:1 molar ratio of solvent; wherein the process is carried out at a pressure and temperature sufficient to convert at least a portion of the dinitrile to a diamine and optionally an aminonitrile.

10. The process of claim 9 wherein the temperature is 50 to 150° C., and the total pressure is about 1.38 to about 10.34 MPa (200 to 1500 psig).

11. The process of claim 10 wherein the catalyst is sponge nickel.

12. The process of claim 11 wherein the modifier is a quaternary ammonium hydroxide compound.

13. The process of claim 12 wherein the modifier is a tetramethylammonium hydroxide.

14. The process of claim 13 wherein the temperature is 70 to 90° C., and the total pressure is about 2.07 to about 6.89 MPa (300 to 1000 psig).

15. The process of claim 14 wherein the modifier is selected from the group consisting of tetramethylammonium hydroxide, tetraethylammonium hydroxide, tetrapropylammonium hydroxide, tetrabutylammonium hydroxide and tetrabutylphosphonium hydroxide.

16. The process of claim 15 wherein the weight ratio of dinitrile to modifier is in the range of about 1:5000 to about 1:50.

* * * * *